(12) United States Patent
Katsuhara et al.

(10) Patent No.: US 12,029,567 B2
(45) Date of Patent: Jul. 9, 2024

(54) BIOPOTENTIAL MEASURING ELECTRODE AND BIOPOTENTIAL MEASURING INSTRUMENT

(71) Applicant: SONY CORPORATION, Tokyo (JP)

(72) Inventors: Mao Katsuhara, Tokyo (JP); Ryo Sasaki, Tokyo (JP)

(73) Assignee: SONY CORPORATION, Tokyo (JP)

( * ) Notice: Subject to any disclaimer, the term of this patent is extended or adjusted under 35 U.S.C. 154(b) by 802 days.

(21) Appl. No.: 17/055,517

(22) PCT Filed: Mar. 25, 2019

(86) PCT No.: PCT/JP2019/012478
§ 371 (c)(1),
(2) Date: Nov. 13, 2020

(87) PCT Pub. No.: WO2019/220776
PCT Pub. Date: Nov. 21, 2019

(65) Prior Publication Data
US 2021/0121113 A1    Apr. 29, 2021

(30) Foreign Application Priority Data
May 16, 2018  (JP) ................................. 2018-094405

(51) Int. Cl.
*A61B 5/268*    (2021.01)
*A61B 5/265*    (2021.01)
(Continued)

(52) U.S. Cl.
CPC .............. *A61B 5/268* (2021.01); *A61B 5/265* (2021.01); *B82Y 30/00* (2013.01); *B82Y 35/00* (2013.01); *B82Y 40/00* (2013.01)

(58) Field of Classification Search
CPC ........... A61B 5/268; A61B 5/265; A61B 5/24; A61B 5/25; B82Y 30/00; B82Y 35/00; B82Y 40/00
See application file for complete search history.

(56) References Cited

U.S. PATENT DOCUMENTS

| 2006/0004273 A1* | 1/2006 | Lobodzinski | A61B 5/28 |
| | | | 600/397 |
| 2010/0261992 A1* | 10/2010 | Axelgaard | A61N 1/0492 |
| | | | 607/152 |

(Continued)

FOREIGN PATENT DOCUMENTS

| JP | 61-501524 A | 7/1986 |
| JP | 2017-073364 A | 4/2017 |

(Continued)

OTHER PUBLICATIONS

Chen, et al., "Soft, Comfortable Polymer Dry Electrodes for High Quality ECG and EEG Recording", Sensors (Basel), vol. 14, No. 12, Dec. 2014, pp. 23758-23780.

(Continued)

*Primary Examiner* — Adam Z Minchella
(74) *Attorney, Agent, or Firm* — CHIP LAW GROUP

(57) ABSTRACT

To achieve both user convenience and measurement accuracy without degrading reliability. A biopotential measuring electrode according to the present disclosure includes at least a portion in contact with a living body, the portion including: a base material resin layer containing a predetermined resin material, rubber, or an elastomer, as a main component; and a conductive particle contained in the base material resin layer, in which the conductive particle includes a predetermined base material particle, and a surface-treated region in which at least a part of a surface of the base material particle is coated or substituted with a predetermined material.

15 Claims, 4 Drawing Sheets

(51) Int. Cl.
*B82Y 30/00* (2011.01)
*B82Y 35/00* (2011.01)
*B82Y 40/00* (2011.01)

(56) References Cited

U.S. PATENT DOCUMENTS

| | | | |
|---|---|---|---|
| 2011/0021899 A1* | 1/2011 | Arps | A61N 1/375 |
| | | | 252/511 |
| 2011/0230749 A1* | 9/2011 | Chan | C08L 83/04 |
| | | | 264/105 |
| 2013/0085368 A1* | 4/2013 | Coggins | A61B 5/25 |
| | | | 600/394 |
| 2017/0251941 A1* | 9/2017 | Hatakeyama | A61B 5/25 |
| 2018/0086948 A1* | 3/2018 | Hatakeyama | C09J 11/06 |
| 2020/0305746 A1* | 10/2020 | Futashima | A61B 5/25 |

FOREIGN PATENT DOCUMENTS

| | | |
|---|---|---|
| JP | 2018-011931 A | 1/2018 |
| KR | 10-2019-0000336 A | 1/2019 |
| WO | 85/004253 A1 | 9/1985 |

OTHER PUBLICATIONS

International Search Report and Written Opinion of PCT Application No. PCT/JP2019/012478, issued on Jun. 18, 2019, 09 pages of ISRWO.

\* cited by examiner

BIOPOTENTIAL MEASURING ELECTRODE AND BIOPOTENTIAL MEASURING INSTRUMENT

CROSS REFERENCE TO RELATED APPLICATIONS

This application is a U.S. National Phase of International Patent Application No. PCT/JP2019/012478 filed on Mar. 25, 2019, which claims priority benefit of Japanese Patent Application No. JP 2018-094405 filed in the Japan Patent Office on May 16, 2018. Each of the above-referenced applications is hereby incorporated herein by reference in its entirety.

TECHNICAL FIELD

The present disclosure relates to a biopotential measuring electrode and a biopotential measuring instrument.

BACKGROUND ART

To measure a potential difference in a living body typified by an electroencephalogram, it is widely practiced to measure a potential difference of interest by attaching an electrode for measuring a biopotential to the living body. Here, to accurately measure a minute potential difference such as the electroencephalogram, it is required to reduce noise superimposed on a potential difference signal via the electrode as much as possible.

In the case of a biopotential measuring instrument (for example, an electroencephalograph) for research applications or medical applications, it is practiced to reduce the noise described above by increasing input impedance of a differential amplifier provided in the measuring instrument. For example, in the applications as described above, an electrode is used that is generally called a wet electrode and for which contact impedance with the living body is reduced by using gel for measurement, physiological saline, or the like.

However, in a biopotential measuring instrument for consumer applications, it is difficult to use the wet electrode as described above, from viewpoints of user contamination, change with time, troublesomeness of wearing, and the like, and it is conceivable that using a dry type electrode called a dry electrode is important. Although such a dry electrode can be mounted relatively easily, the contact impedance with the living body is as large as 10 kΩ to 100 kΩ (0.1 MΩ), and variation between measurement sites (electrodes) are also large. That is, the noise component as described above increases, and there is a concern about degradation of signal quality. For that reason, efforts have conventionally been practiced to reduce contact resistance between the dry electrode and the living body.

For example, in Non-Patent Document 1 below, to achieve both good feeling of wearing felt by a person to be measured and measurement accuracy, an electrode has been devised in which a conductive particle such as carbon is mixed with an elastomer such as rubber and that is rich in flexibility and comfortable to wear. Furthermore, in Patent Document 1 below, to reduce the contact impedance, a bioelectrode has been devised in which a functional material that is a particle whose surface is coated with gold, silver, or platinum is contained in a resin layer.

CITATION LIST

Patent Document

Patent Document 1: Japanese Patent Application Laid-Open No. 2018-11931

Non-Patent Document

Non-Patent Document 1: Y. H. Chen et al., "Soft, Comfortable Polymer Dry Electrodes for High Quality ECG and EEG Recording", Sensors, 2014, 14, 23758-23780.

SUMMARY OF THE INVENTION

Problems to be Solved by the Invention

However, as a result of verification by the present inventors, it has become clear that it is difficult to reduce the contact impedance between the living body and the electrode with the technology devised in Non-Patent Document 1 described above. Furthermore, in a case where the technology devised in Patent Document 1 described above is used, there is a possibility that mechanical reliability is degraded such that, for example, the electrodes are peeled off due to degradation of adhesion, and also mass production is difficult.

As described above, there is a need for a biopotential measuring electrode capable of achieving both the user convenience and the measurement accuracy without degrading the adhesion to the living body.

Thus, in the present disclosure, a biopotential measuring electrode and a biopotential measuring instrument are devised capable of achieving both the user convenience and the measurement accuracy without degrading the adhesion to the living body.

Solutions to Problems

According to the present disclosure, a biopotential measuring electrode is provided including at least a portion in contact with a living body, the portion including: a base material resin layer containing a predetermined resin material, rubber, or an elastomer, as a main component; and a conductive particle contained in the base material resin layer, in which the conductive particle includes a predetermined base material particle, and a surface-treated region in which at least a part of a surface of the base material particle is coated or substituted with a predetermined material and that exhibits conductivity.

Furthermore, according to the present disclosure, a biopotential measuring instrument is provided including at least the biopotential measuring electrode described above.

According to the present disclosure, the biopotential measuring electrode includes the base material resin layer containing a predetermined resin material, rubber, or an elastomer, as a main component, so that adhesion to the living body is not degraded, and the user convenience is improved. Furthermore, the conductive particle is contained in such a base material resin layer, so that the contact impedance is lowered and the measurement accuracy is improved.

Effects of the Invention

As described above, according to the present disclosure, it is possible to achieve both the user convenience and the measurement accuracy without degrading the adhesion to the living body.

Note that, the above-described effect is not necessarily limited, and, in addition to the above effect, or in place of the above effect, any of effects described in this specification, or other effects that can be grasped from the present specification may be exhibited.

MODE FOR CARRYING OUT THE INVENTION

Figure 1:
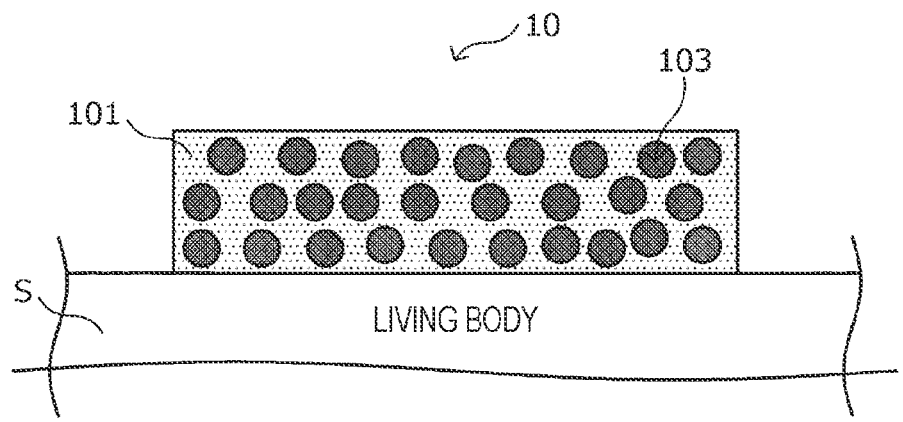
FIG. 1 is an explanatory diagram schematically illustrating an example of a configuration of a biopotential measuring electrode according to an embodiment of the present disclosure.

Hereinafter, preferred embodiments of the present disclosure will be described in detail with reference to the accompanying drawings. Note that, in the present specification and the drawings, components having substantially the same functional configuration are denoted by the same reference signs, and redundant explanations will be omitted.

Note that, the description will be given in the following order.
1. Embodiment
1.1. Biopotential measuring electrode
1.2. Method of manufacturing biopotential measuring electrode
1.3. Biopotential measuring instrument
2. Examples As briefly mentioned earlier, in the measuring instrument for measuring the minute potential difference such as an electroencephalogram, for example, the measurement accuracy is largely affected by the noise generated due to the fact that electromagnetic waves in an external environment couples with a human body and wiring lines and enter. The influence of such noise is called alternating current interference. Among such alternating current interferences, the one caused by electrostatic induction with the human body occurs when a voltage generated in the living body is input through an electrode. Since such a voltage is almost the same in the living body, it is usually reduced by a differential amplifier provided in the measuring instrument. However, if a difference occurs in contact impedance between the electrode connected to the differential amplifier and the living body, a difference occurs in an input unit of the differential amplifier, and the voltage cannot be removed during differential amplification and a lot of noise is superimposed. A magnitude $V_{noise}$ of the noise is expressed as the following formula (1) by using a contact impedance $Z_n$ (n=1, 2, ... ) at an electrode n, an input impedance $Z_{in}$ of the differential amplifier, and an input signal voltage $V_{sig}$.

[Expression 1]

$$V_{noise} \approx \frac{Z_1 - Z_2}{Z_{in}} \cdot V_{sig} \qquad \text{Formula (1)}$$

As is clear from the formula (1) described above, it can be seen that the magnitude of the noise is proportional to the impedance difference in the input unit. From this fact, it can be seen that it is important to reduce the contact impedance with the living body to improve the measurement accuracy when measuring a minute potential difference.

The present inventors have conducted intensive studies on a method for reducing the contact impedance with the living body, and resultantly have found to manufacture an electrode by using a base material resin containing a conductive particle having a specific structure, and have devised a biopotential measuring electrode according to an embodiment of the present disclosure as described below.

Hereinafter, the biopotential measuring electrode according to the embodiment of the present disclosure will be described in detail.

EMBODIMENT

<Biopotential Measuring Electrode>

Hereinafter, the biopotential measuring electrode according to the embodiment of the present disclosure will be described in detail with reference to FIGS. 1, 2A, 2B, 2C, 3, 4A, 4B, and 4C.

Figure 2A:
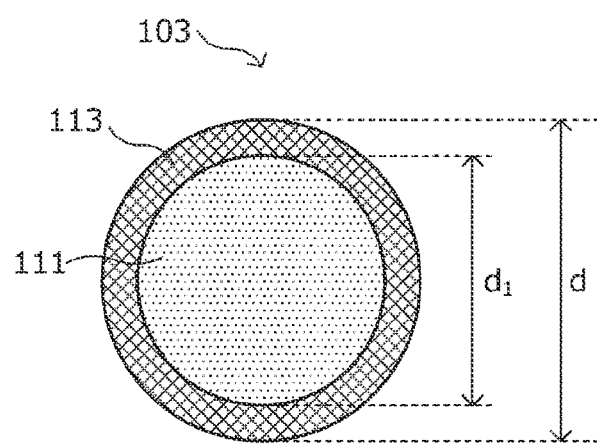
FIG. 2A is an explanatory diagram for explaining a conductive particle contained in the biopotential measuring electrode according to the embodiment.
Figure 2B:
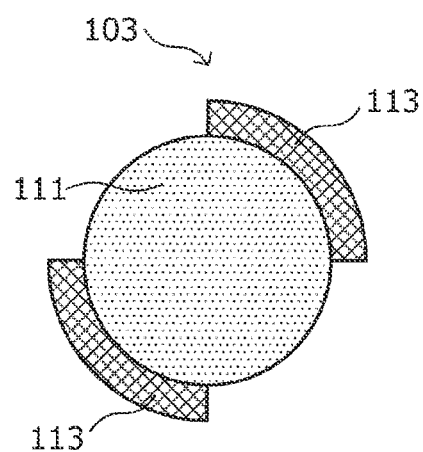
FIG. 2B is an explanatory diagram for explaining the conductive particle contained in the biopotential measuring electrode according to the embodiment.
Figure 2C:
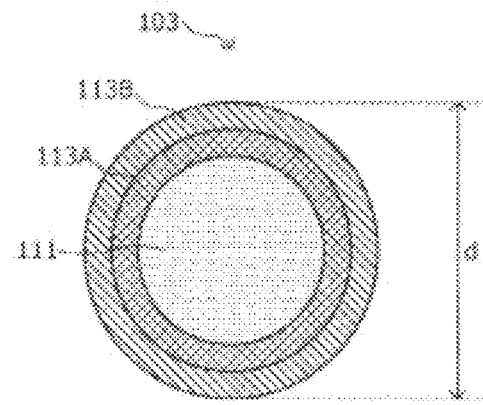
FIG. 2C is an explanatory diagram for explaining the conductive particle contained in the biopotential measuring electrode according to the embodiment.

FIG. 1 is an explanatory diagram schematically illustrating an example of a configuration of the biopotential measuring electrode according to the present embodiment. FIGS. 2A, 2B, and 2C are explanatory diagrams for explaining the conductive particle contained in the biopotential measuring electrode according to the present embodiment. FIGS. 3, 4A, 4B, and 4C are explanatory diagrams for explaining the biopotential measuring electrode according to the present embodiment.

The biopotential measuring electrode according to the present embodiment is an electrode used for measuring a minute potential difference generated inside a living body, such as an electroencephalogram or the like, for example. In such a biopotential measuring electrode 10, as schematically illustrated in FIG. 1 as an example, at least a portion in contact with a living body, of the biopotential measuring electrode 10 includes: a base material resin layer 101 containing a predetermined resin material, rubber, or an elastomer, as a main component; and conductive particles 103 contained in the base material resin layer 101.

[Base Material Resin Layer 101]

The base material resin layer 101 is a layer containing a predetermined resin material, rubber, or an elastomer, as a main component. In more detail, the base material resin layer 101 according to the present embodiment is a layer including a solidified product or a cured product of a resin component containing a predetermined resin material, rubber, or an elastomer, as a main component. Here, the term "solidified product" simply means a product in which the resin component itself is solidified, and the term "cured product" means a product in which the resin component contains various curing agents and is cured. Furthermore, the "main component" means a component contained in greater than or equal to 50 parts by mass of 100 parts by mass of all resin components, and the "resin component" does not include a non-resin component such as a crosslinking agent.

In the biopotential measuring electrode 10 according to the present embodiment, at least the portion in contact with the living body includes the base material resin layer 101 as described above, whereby it is possible to hold adhesion with the living body even if various movements such as a body movement due to the daily life of a wearer of the electrode occur in the living body.

Here, a volume resistivity value of the base material resin layer 101 is preferably, for example, less than or equal to 100 kΩ·cm. The volume resistivity value of the base material resin layer 101 is less than or equal to 100 kΩ·cm, whereby it is possible to more reliably improve the measurement accuracy of the potential difference (hereinafter, referred to as "biopotential") generated in the living body. The volume resistivity value of the base material resin layer 101 is more preferably on the order of less than or equal to several kΩ·cm. Here, the base material resin layer 101 according to the present embodiment is preferably an insulating layer having the volume resistivity value as described above, but may exhibit conductivity. Note that, the volume resistivity value of the base material resin layer 101 can be measured according to the method described in JIS K6271:2008.

Furthermore, the base material resin layer 101 preferably has a predetermined flexibility so that the base material resin layer 101 can follow a movement such as the body movement even in a case where such a movement occurs in the living body to which the base material resin layer 101 is attached. Examples of a parameter indicating the flexibility of the base material resin layer 101 include various parameters such as Shore hardness and elastic modulus of the base material resin layer 101.

For example, the base material resin layer 101 according to the present embodiment preferably has a Shore hardness of less than or equal to 90 HS. The Shore hardness of the base material resin layer 101 is less than or equal to 90 HS, whereby it is possible to follow the movement such as the body movement occurring in the living body as described above, and it is possible to further improve the adhesion with the living body, and thus the measurement accuracy can be further improved. Note that, the Shore hardness of the base material resin layer 101 can be measured according to the method described in JIS K6253:2012.

Examples of the resin material constituting the base material resin layer 101 as described above include a thermoplastic resin selected from the group consisting of polyvinyl chloride resin, polypropylene resin, polyethylene resin, polyurethane resin, polyacetal resin, polyamide resin, polycarbonate resin, and copolymers thereof.

Furthermore, examples of the rubber constituting the base material resin layer 101 as described above include natural rubber, and various synthetic rubbers represented by diene rubbers such as styrene-butadiene rubber and isoprene rubber.

Furthermore, examples of the elastomer constituting the base material resin layer 101 as described above include a thermosetting elastomer selected from the group consisting of silicone resin and polyurethane resin.

Note that, the resin materials, rubbers, and elastomers as described above are merely examples, and various known resin materials, rubbers, and elastomers can be used other than the materials described above.

Furthermore, the base material resin layer 101 according to the present embodiment may contain various additives, for example, pigments, colorants, and the like, as long as the physical properties of the base material resin layer 101 are not impaired.

[Conductive Particle 103]

The conductive particles 103 are contained in the base material resin layer 101 as described above, and cause the conductivity of the biopotential measuring electrode 10 according to the present embodiment to exhibit. As schematically illustrated in FIG. 2A, such a conductive particle 103 includes a predetermined base material particle 111, and a surface-treated region 113 in which at least a part of the surface of such a base material particle 111 is coated or substituted and that exhibits conductivity.

The base material particle 111 functions as a carrier for the surface-treated region 113. As such a base material particle 111, for example, various polymer particles, carbon particles, or metal particles can be used.

The polymer particles are particles including various resin compositions, and examples thereof include particles of polyphenylene sulfide (PPS) resin, polyethylene terephthalate (PET) resin, polyether sulfone (PES) resin, polyamide imide (PAI) resin, acrylic resin, polyvinylidene difluoride (PVDF) resin, epoxy resin, polylactic acid resin, nylon resin, urethane resin, and the like.

The carbon particles are particles including various carbon compounds, and examples thereof include particles of carbon black (graphite), carbon nanotube, and graphene, granules of flakes or fibers of these substances, and the like.

The metal particles are particles including various metals, and examples thereof include gold particles, silver particles, copper particles, and the like.

The polymer particles, carbon particles, and metal particles as described above are merely examples, and known particles can be used other than the particles exemplified above.

Here, as the base material particle 111 according to the present embodiment, it is preferable to use the one in which the base material particle itself exhibits conductivity, such as the carbon particles, and the metal particles. As a result, the conductivity of the biopotential measuring electrode 10 according to the present embodiment can be more reliably ensured. Furthermore, in a case where a polymer particle is used as the base material particle 111, the flexibility of the biopotential measuring electrode 10 can be improved.

An average particle diameter (an average primary particle diameter, a length $d_1$ in FIG. 2A) of the base material particle 111 as described above is preferably, for example, within a range of from 10 to 100 nm. The average primary particle diameter $d_1$ of the base material particle 111 is within the range described above, whereby the conductive particles 103 are more easily dispersed in the base material resin layer 101, and the measurement accuracy can be further improved. The average primary particle diameter $d_1$ of the base material particle 111 is more preferably within a range of from 10 to 50 nm.

Furthermore, an average secondary particle diameter of the base material particle 111 is preferably within a range of from 30 to 500 nm. The base material particle 111 has the secondary particle diameter that falls within the range described above, whereby the conductive particles 103 are more easily dispersed in the base material resin layer 101, and the measurement accuracy can be further improved.

Here, the average primary particle diameter and the average secondary particle diameter of the base material particle 111 can be measured by direct observation by a transmission electron microscope (TEM), or by particle diameter measurement by a dynamic light scattering method.

The surface-treated region 113 is a region provided for the conductive particle 103 to exhibit conductivity even if the base material particle 111 is a particle that does not have conductivity. The surface-treated region 113 is preferably present over the entire surface of the base material particle 111 as schematically illustrated in FIG. 2A, but is only required to be present in at least a part of the surface of the base material particle 111 as schematically illustrated in FIG. 2B.

The surface-treated region 113 may be a surface-coated region in which at least a part of the surface of the base material particle 111 is coated, or may be a surface-modified region in which at least a part of the surface of the base material particle 111 is substituted with a predetermined substituent. At least a part of the surface of the base material particle 111 is coated or modified with a predetermined substance and becomes the surface-treated region 113, whereby the conductive particle 103 according to the present embodiment exhibits excellent conductivity.

In a case where, as the surface-treated region 113, a surface-coated region is provided in which at least a part of the surface of the base material particle 111 is coated with a predetermined conductive material, the conductive material for coating at least the part of the surface of the base material particle 111 is preferably an organic conductive polymer or a metal compound.

As the organic conductive polymer, it is possible to use various known organic conductive polymers, and as such an organic conductive polymer, for example, it is possible to use at least one selected from the group consisting of PEDOT-PSS, polypyrrole, polyacetylene, polyphenylene vinylene, polythiophene, polythiol, polyaniline, and analogs thereof. These conductive polymers may be used alone or in combination. Furthermore, it is also possible to use a copolymer of the conductive polymers as described above.

Moreover, in a case where the organic conductive polymer is used as the conductive material, to more reliably coat the surface of the base material particle 111 and improve the adhesion between the base material particle 111 and the organic conductive polymer, various binder resins may be mixed, such as water-soluble acrylic resin, water-soluble urethane resin, water-soluble polyester alkyd, and water-soluble amino resin, in addition to the organic conductive polymer described above.

Furthermore, as the metal compound, various known metal compounds can be used, and as such a metal compound, for example, it is possible to use, for example, at least one of a sulfide, a selenide, or a chloride of gold, silver, or copper. In such a case, if a copper compound such as copper sulfide, copper selenide, copper chloride, or copper oxide, a silver compound such as silver chloride, silver sulfide, or silver selenide, or the like is used, it is possible to further reduce the manufacturing cost of the biopotential measuring electrode 10, which is more preferable.

Moreover, to implement the surface-treated region (in more detail, the surface-coated region) according to the present embodiment, the organic conductive polymer and the metal compound as described above may be used in combination.

In a case where, as the surface-treated region 113, a surface-modified region is provided in which at least a part of the surface of the base material particle 111 is substituted with a predetermined substituent, at least a part of the surface of the base material particle 111 is preferably sulfurized, selenized, or chlorinated by being treated with a predetermined compound. In particular, such surface modification treatment is useful in a case where the base material particle 111 is a metal particle.

In the conductive particle 103 according to the present embodiment, the number of layers of the surface-treated region 113 as described above is not limited to one layer, and for example, a plurality of layers of the surface-treated region 113 may be provided as illustrated in a case where the surface-treated region 113 is provided for two layers in FIG. 2C (surface-treated regions 113A and 113B). For example, a plurality of the surface-treated regions 113 may be provided that uses organic conductive polymers or metal compounds different from each other, or the surface-treated region 113 using an organic conductive polymer and the surface-treated region 113 using a metal compound may be laminated. Furthermore, it is also possible to modify at least a part of the surface of the base material particle 111 and then coat the modified surface with an organic conductive polymer or a metal compound. As a result, for example, it is possible to implement the conductive particle 103 in which a silver particle is used as the base material particle 111, and on the surface of such a silver particle, a surface-treated region using silver chloride that is a type of the metal compound, and a surface-treated region using PEDOT-PSS that is a type of the conductive polymer are present as the surface-treated region 113.

Subsequently, a specific combination will be briefly described of the base material particle 111 and the surface-treated region 113 in the conductive particle 103 according to the present embodiment. In the conductive particle 103 according to the present embodiment, as combinations of the base material particle 111 and the surface-treated region 113, those indicated in Table 1 below are conceivable, for example. Note that, configuration examples of the conductive particle 103 illustrated in Table 1 below are merely examples, and the conductive particle 103 according to the present embodiment is not limited to the configuration examples described below.

TABLE 1

| | Configuration example of conductive particle | | |
|---|---|---|---|
| | Base material | Surface-treated region 113 | |
| No. | particle 111 | Form | Substance |
| 1 | Metal particle | Surface-coated | Conductive polymer |
| 2 | Carbon particle | Surface-coated | Conductive polymer |
| 3 | Polymer particle | Surface-coated | Conductive polymer |
| 4 | Metal particle | Surface-coated | Metal compound |
| 5 | Metal particle | Surface-modified | Metal compound |

Note that, in a case where a carbon particle is used as the base material particle 111, a surface-modified carbon particle may be used in which a predetermined modifying group is introduced on the surface of the carbon particle to further strengthen the adhesion between the conductive polymer or the metal compound and the carbon particle. Such a modifying group is introduced on the surface of the carbon particle by treating the surface of the carbon particle with a predetermined compound. Examples of such a compound include triisostearoyl titanate coupling agents, silane coupling agents, various thiol compounds, various phosphoric acid esters, and the like.

Here, the thickness of the surface-treated region 113 as described above is preferably within a predetermined range for the conductive particle 103 to exhibit more excellent conductivity. Specifically, in a case where the surface-treated region 113 is implemented by using a conductive polymer, the thickness of the surface-treated region 113 is preferably within a range of from about 10 to 100 nm, for example, and in a case where the surface-treated region 113 is implemented by using a metal compound, the thickness of the surface-treated region 113 is preferably within a range of from about 5 nm to 100 nm, for example. The thickness of the surface-treated region 113 is set within the range as described above, whereby the conductive particle 103 according to the present embodiment exhibits more excellent conductivity.

[Average Particle Diameter of Conductive Particle 103]

An average particle diameter (for example, the length d in FIG. 2A or 2C) of the conductive particle 103 including the base material particle 111 and the surface-treated region 113 as described above is preferably within a range of from 15 to 500 nm. The average particle diameter d of the conductive particles 103 is within the range described above, whereby the conductive particles 103 are more easily dispersed in the base material resin layer 101, and the measurement accuracy can be further improved. The average particle diameter d of the conductive particle 103 is more preferably within a range of from 15 to 200 nm. Note that, the average particle diameter d of the conductive particle 103 can be measured by a method similar to that of the average primary particle diameter $d_1$ of the base material particle 111.

[Content of Conductive Particles 103]

Subsequently, the content of the conductive particles 103 in the base material resin layer 101 will be described.

In the biopotential measuring electrode 10 according to the present embodiment, to further improve the measurement accuracy, the content of the conductive particles 103 in the base material resin layer 101 is preferably within a predetermined range.

Here, the preferable content of the conductive particles 103 in the base material resin layer 101 varies depending on a type (in more detail, specific gravity or the like) of the base material resin layer 101, a type (in more detail, specific gravity or the like) of the base material particle 111, and the like.

For example, in a case where a carbon particle is used as the base material particle 111, regardless of the type of the base material resin layer 101, the content of the conductive particles 103 in the base material resin layer 101 is preferably within a range of from about 5 to 40% by mass, and more preferably within a range of from about 10 to 30% by mass, with respect to the total mass of the base material resin layer 101 and the conductive particles 103.

Furthermore, in a case where a polymer particle is used as the base material particle 111, the content of the conductive particles 103 in the base material resin layer 101 is preferably within a range of from about 5 to 40% by mass, and more preferably within a range of from about 10 to 30% by mass.

Moreover, in a case where a metal particle is used as the base material particle 111, the content of the conductive particles 103 in the base material resin layer 101 is preferably within a range of from about 30 to 80% by mass.

Note that, in a case where the content of the conductive particles 103 in the base material resin layer 101 is to be measured afterwards, measurement is possible by using a measurement method by observation and image analysis with a scanning electron microscope (SEM), a measurement method by elemental analysis such as a combustion method or inductively coupled plasma (ICP) emission spectroscopic analysis, or the like.

As described above, in the biopotential measuring electrode 10 according to the present embodiment, the conductive particles 103 exhibiting conductivity not only are present on the electrode surface, but also are contained in the base material resin layer 101, so that it is possible to easily prevent that the conductivity is lowered due to peeling off of the conductive particles 103, or the like. Furthermore, since the conductive particles 103 are dispersed in the base material resin layer 101, it is possible to achieve excellent conductivity as the entire electrode while suppressing the amount of the conductive substance used to implement the surface-treated region 113.

Note that, the thickness of the biopotential measuring electrode 10 according to the present embodiment is not particularly limited, but can be, for example, about 0.5 mm to 2 cm.

Furthermore, in the biopotential measuring electrode 10 according to the present embodiment, the portion in contact with the living body includes a resin (base material resin layer 101) containing the conductive particles 103, so that it is possible to sufficiently reduce the noise component by the differential amplification and acquire high-quality data even if the contact impedance between the electrode and the living body changes dynamically due to the body movement in daily life, or the like.

The biopotential measuring electrode 10 according to the present embodiment as described above is further provided with a wiring line (not illustrated) for taking out electrical information such as a minute potential difference caused by the living body, a connection terminal (not illustrated) for connecting the biopotential measuring electrode 10 to a measuring device, and the like, which are used for actual measurement.

Modifications

Figure 3:
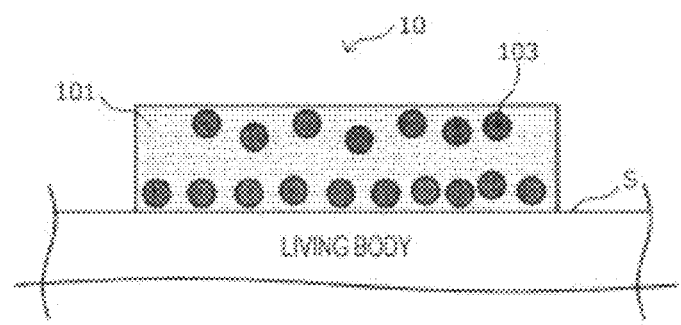
FIG. 3 is an explanatory diagram for explaining the biopotential measuring electrode according to the embodiment.

In the biopotential measuring electrode 10 according to the present embodiment, the conductive particles 103 may be uniformly dispersed in the base material resin layer 101, but, for example, as schematically illustrated in FIG. 3, the conductive particles 103 may be unevenly distributed in the base material resin layer 101 so that more conductive particles 103 are distributed in the base material resin layer 101 on a side closer to a living body S. As described below, the biopotential measuring electrode 10 according to the present embodiment is manufactured, for example, by injection-molding a resin (resin to be the base material resin layer 101) in which the conductive particles 103 are kneaded into a desired shape. For example, the uneven distribution state of the conductive particles 103 as illustrated in FIG. 3 can be implemented by performing injection molding using a known method, for example, two-color molding, or the like.

Figure 4A:
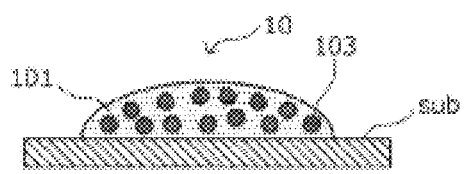
FIG. 4A is an explanatory diagram for explaining the biopotential measuring electrode according to the embodiment.
Figure 4B:
FIG. 4B is an explanatory diagram for explaining the biopotential measuring electrode according to the embodiment.
Figure 4C:
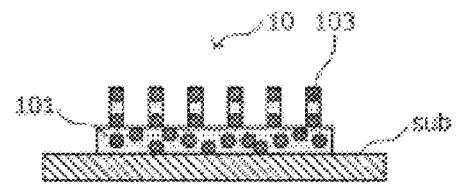
FIG. 4C is an explanatory diagram for explaining the biopotential measuring electrode according to the embodiment.

Furthermore, the shape of the biopotential measuring electrode 10 according to the present embodiment may have a planar shape as schematically illustrated in FIG. 1 or the like, or may have any other shapes. For example, as schematically illustrated in FIG. 4A, the biopotential measuring electrode 10 may be provided in a dome shape on a planar substrate sub, or as schematically illustrated in FIG. 4B, the biopotential measuring electrode 10 may be provided in a pyramid shape on the planar substrate sub. Furthermore, as schematically illustrated in FIG. 4C, the biopotential measuring electrode 10 may be provided in a comb shape on the planar substrate sub.

In the above, the biopotential measuring electrode 10 according to the present embodiment has been described in detail.

<Method of Manufacturing Biopotential Measuring Electrode>

Subsequently, a method will be briefly described of manufacturing the biopotential measuring electrode 10 according to the present embodiment as described above.

The biopotential measuring electrode 10 according to the present embodiment can be manufactured by using a so-called injection molding technology. The manufacturing process, for example, includes: a step of manufacturing the conductive particles 103; a step of manufacturing a conductive resin composition by kneading the manufactured conductive particles 103 into a resin composition to be the base material resin layer 101; and a step of manufacturing a biopotential measuring electrode by injection-molding the manufactured conductive resin composition.

Here, the method of manufacturing the conductive particles 103 is not particularly limited, and it is only required to adopt a known method such as causing a compound for forming the surface-treated region 113 to permeate into a container filled with the base material particles 111, or adding the base material particles 111 to a solution containing the compound for forming the surface-treated region 113 and stirring the solution. The method of manufacturing the conductive resin composition is also not particularly limited, and the method can be performed by a known method.

Furthermore, the method of injection-molding the manufactured conductive resin composition is not particularly limited, and a biopotential measuring electrode having an arbitrary shape can be manufactured in accordance with various known injection-molding technologies. At this time, as mentioned earlier, by using a method such as two-color molding, it is also possible to manufacture the biopotential measuring electrode 10 in which the conductive particles 103 are unevenly distributed, as illustrated in FIG. 3, for example.

As described above, in the method of manufacturing the biopotential measuring electrode according to the present embodiment, since the biopotential measuring electrode is manufactured by using the injection molding technology as described above, the biopotential measuring electrodes having various shapes can be easily manufactured.

In the above, the method of manufacturing the biopotential measuring electrode according to the present embodiment has been briefly described.

<Biopotential Measuring Instrument>

Next, a biopotential measuring instrument will be briefly described that includes the biopotential measuring electrode according to the present embodiment.

The biopotential measuring instrument according to the present embodiment is not particularly limited as long as the biopotential measuring instrument includes the biopotential measuring electrode 10 according to the present embodiment, and may be an analog biopotential measuring instrument, or may be a digital biopotential measuring instrument. Furthermore, a biopotential to be measured is not particularly limited, and various biopotentials such as an electrocardiogram, an electromyogram, an electroencephalogram, and an electrodermal activity can be measurement targets.

Figure 5:
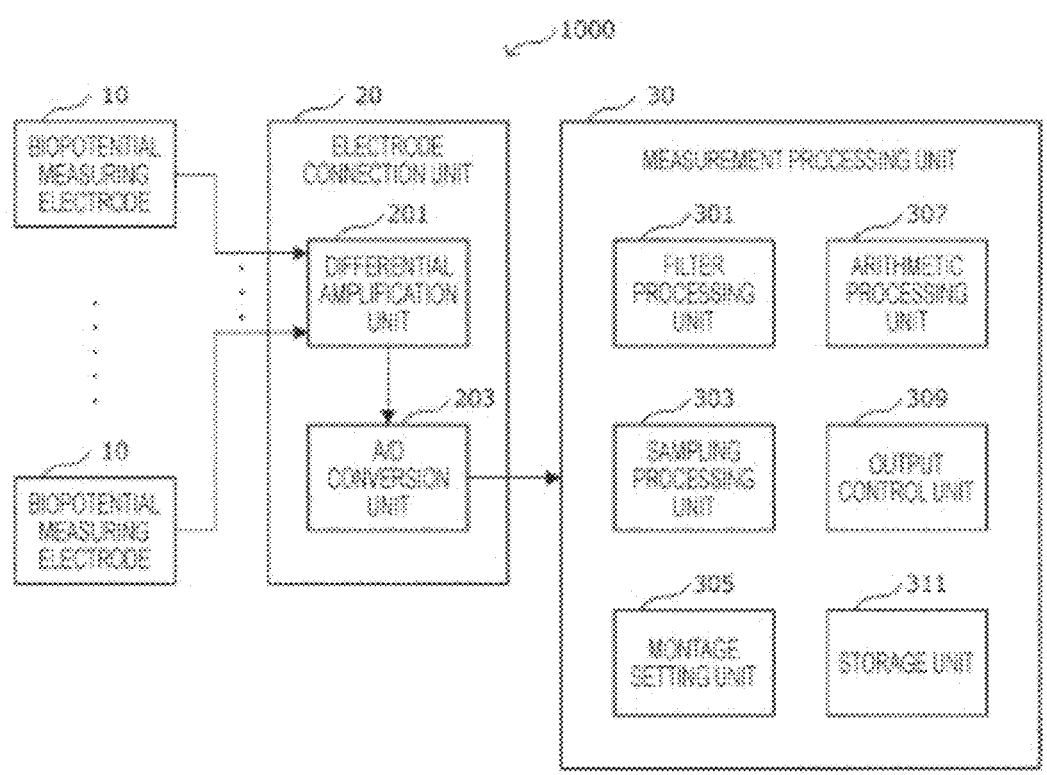
FIG. 5 is a block diagram schematically illustrating an example of a configuration of a biopotential measuring instrument according to the embodiment.

Hereinafter, a digital electroencephalograph will be briefly described as an example of the biopotential measuring instrument according to the present embodiment, with reference to FIG. 5.

A biopotential measuring instrument 1000 according to the present embodiment includes at least the biopotential measuring electrode 10 as described earlier. Such a biopotential measuring instrument 1000 includes an electrode connection unit 20 and a measurement processing unit 30, as illustrated in FIG. 5, for example, other than such a biopotential measuring electrode 10.

The electrode connection unit 20 is a unit to which one or a plurality of the biopotential measuring electrodes 10 is connected, and includes a connector that is paired with a connection terminal provided on the biopotential measuring electrode 10. The electrode connection unit 20 includes a differential amplification unit 201 and an A/D conversion unit 203, as illustrated in FIG. 5, for example.

The differential amplification unit 201 is implemented by a known differential amplification circuit, and is caused to differentially amplify the strength of the biopotential collected by the biopotential measuring electrode 10. As a result, the strength of a minute biopotential collected by the biopotential measuring electrode 10 is amplified, and the minute biopotential can be measured more reliably. The biopotential differentially amplified by the differential amplification unit 201 is converted into a digital signal by the A/D conversion unit 203 in the subsequent stage, and output to the measurement processing unit 30.

The measurement processing unit 30 is a unit that measures the biopotential by using digitized potential information regarding the biopotential. In a case where an electroencephalogram is measured as an example of the biopotential, the measurement processing unit 30 includes a filter processing unit 301, a sampling processing unit 303, a montage setting unit 305, an arithmetic processing unit 307, an output control unit 309, and a storage unit 311, as illustrated in FIG. 5, for example. These processing units cooperate with each other, whereby a measured value of the biopotential of interest (that is, the electroencephalogram) is extracted from the potential information.

The filter processing unit 301 is implemented by, for example, a central processing unit (CPU), a read only memory (ROM), a random access memory (RAM), and the like. The filter processing unit 301 performs various types of known filtering processing on the potential information regarding the biopotential output from the electrode connection unit 20. As a result, for example, potential information belonging to a specific frequency band can be extracted.

The sampling processing unit 303 is implemented by, for example, a CPU, ROM, RAM, and the like. The sampling processing unit 303 extracts information at predetermined intervals by a known method from the potential information regarding the biopotential subjected to the filtering processing. The extracted potential information is stored in the storage unit 311 or the like described later as needed in association with time information regarding the time when the potential information is acquired.

The montage setting unit 305 is implemented by, for example, a CPU, ROM, RAM, and the like. The montage setting unit 305 sets an implementation condition when montage processing is performed for extracting a potential difference of interest from the potential information stored in the storage unit 311 or the like. Information regarding the set implementation condition of the montage processing is used by the arithmetic processing unit 307.

The arithmetic processing unit 307 is implemented by, for example, a CPU, ROM, RAM, and the like. The arithmetic processing unit 307 performs arithmetic processing of calculating the potential difference of interest by using the potential information stored in the storage unit 311 or the like, and the information regarding the implementation condition of the montage processing set by the montage setting unit 305. As a result, a significant potential difference (an electroencephalogram in this example) is calculated from the potential information collected by the biopotential measuring electrode 10. The arithmetic processing unit 307 may store the information regarding the calculated biopotential in the storage unit 311 or the like as history information.

The output control unit 309 is implemented by, for example, a CPU, ROM, RAM, output device, communication device, and the like. The output control unit 309 performs output control for displaying the information regarding the biopotential calculated by the arithmetic processing unit 307 (information regarding the electroencephalogram, in this example) on a display provided in the biopotential measuring instrument 1000 and/or a display provided outside the biopotential measuring instrument 1000. Furthermore, the output control unit 309 can also output the information regarding the biopotential calculated by the arithmetic processing unit 307 as a paper medium, or perform output control when outputting electronic data of the information on the biopotential calculated by the arithmetic processing unit 307 to various external information processing devices.

The storage unit 311 is implemented by, for example, a RAM, various storage devices, or the like. Various types of information such as the potential information regarding the biopotential and the information regarding the calculated biopotential are appropriately recorded in the storage unit 311. Furthermore, in the storage unit 311, various types of setting information regarding the measurement processing unit 30, various parameters and progress of processing that need to be saved when the measurement processing unit 30 performs some processing, and the like, or various databases, programs, and the like are recorded appropriately. On the storage unit 311, the filter processing unit 301, the sampling processing unit 303, the montage setting unit 305, the arithmetic processing unit 307, the output control unit 309, and the like can freely perform data read/write processing.

In the above, an example has been described of functions of the biopotential measuring instrument 1000 according to the present embodiment that functions as an electroencephalograph. Each of the components described above may be configured using a general-purpose member or circuit, or may be configured by hardware specialized for the function of each component. Furthermore, the function of each component may be entirely performed by the CPU or the like. Thus, it is possible to change the configuration to be used as appropriate depending on the technical level of each implementation of the present embodiment.

Note that, it is possible to create a computer program for implementing each function of the measurement processing unit 30 according to the present embodiment as described above, and install the computer program in a personal computer or the like. Furthermore, it is also possible to provide a computer readable recording medium in which such a computer program is stored. The recording medium is, for example, a magnetic disk, an optical disk, a magneto-optical disk, a flash memory, or the like. Furthermore, the above computer program may be distributed via, for example, a network without using a recording medium.

In the above, the biopotential measuring instrument according to the present embodiment has been briefly described with reference to FIG. 5 by taking the electroencephalograph as an example.

EXAMPLES

Hereinafter, the biopotential measuring electrode according to the present disclosure will be specifically described with reference to examples and comparative examples. Note that, the examples described below are merely examples of the biopotential measuring electrode according to the present disclosure, and the biopotential measuring electrode according to the present disclosure is not limited to the examples described below.

Test Example 1

First, a PEDOT-PSS (manufactured by Sigma-Aldrich, Inc.) aqueous solution is caused to permeate through a tube filled with conductive carbon black (TOKABLACK manufactured by TOKAI CARBON CO., LTD., average primary particle diameter (catalog value): 25 nm), to coat the surface of the carbon black with PEDOT-PSS. Subsequently, the particles obtained as described above were dried in a vacuum oven to manufacture conductive particles including carbon particles (carbon black) as the base material particles and a PEDOT-PSS coating layer as the surface-treated region. When the average particle diameter of the obtained conductive particles was measured, it was found to be 30 nm, so that the thickness of PEDOT-PSS was found to be about 5 nm.

The conductive particles obtained as described above were kneaded with a thermoplastic polyurethane elastomer (RESAMINE P manufactured by Dainichiseika Color & Chemicals Mfg. Co., Ltd.) so that the content was 30% by mass, to obtain a conductive elastomer. The obtained elastomer was injection-molded to obtain a flat biopotential measuring electrode having a size of 1 cm×1 cm×0.2 cm. The impedance characteristic of the obtained biopotential measuring electrode was measured by using an impedance measuring instrument (CompactStat.h manufactured by Ivium Technologies).

Furthermore, as a comparison, the impedance characteristic of a general Ag/AgCl electrode and the impedance characteristic of a biopotential measuring electrode manufactured similarly as described above by using carbon black (TOKABLACK described above) not coated with PEDOT-PSS were separately measured by using the impedance measuring instrument described above.

Figure 6:
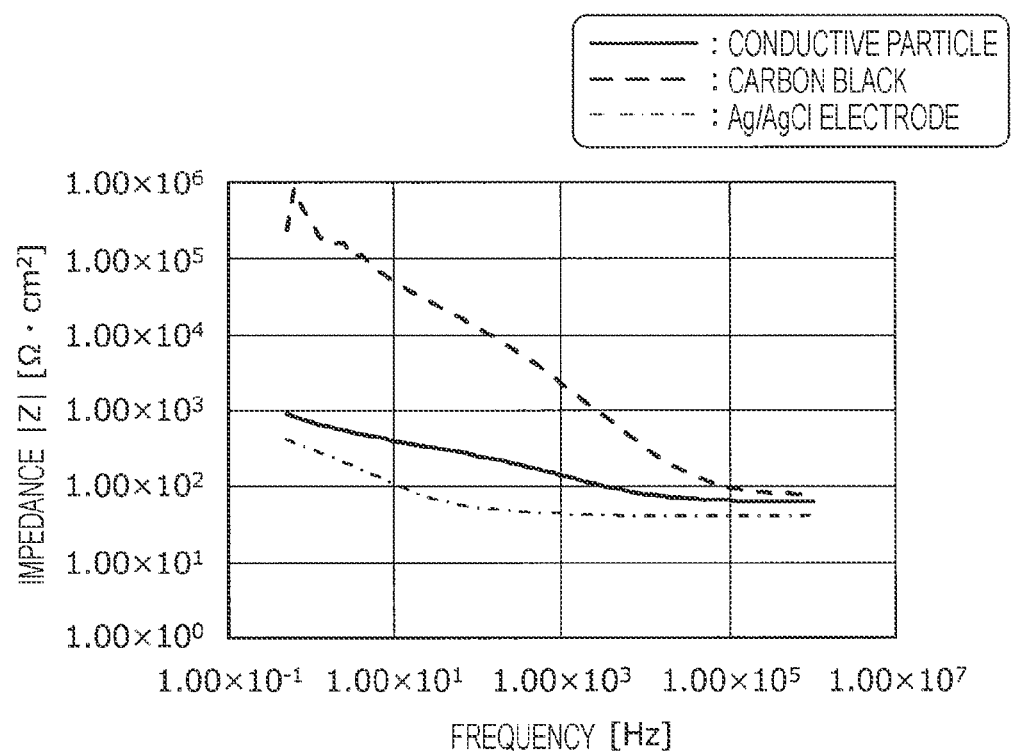
FIG. 6 is a graph illustrating impedance measurement results in an experimental example.

The obtained results are indicated together in FIG. 6. In FIG. 6, the horizontal axis represents the frequency [Hz], and the vertical axis represents the measured value of impedance $|Z| [\Omega \cdot cm^2]$.

As is clear from FIG. 6, the impedance of the biopotential measuring electrode corresponding to the example of the present disclosure in which the conductive particles are present in the thermoplastic polyurethane resin is an extremely low value as compared with the impedance of the carbon black, and it can be seen that, in particular, in the low frequency region of less than or equal to 40 Hz that is equivalent to the frequency of the electroencephalogram, the impedance can be reduced to the same level as the Ag/AgCl electrode used as a reference electrode. For example, in the measurement results illustrated in FIG. 6, the impedance $|Z|$ at 10 Hz was 109 Ω·cm$^2$ for the Ag/AgCl electrode, whereas the impedance was 50146 Ω·cm$^2$ for the biopotential measuring electrode using the elastomer containing carbon black, and 406 Ω·cm$^2$ for the biopotential measuring electrode using an elastomer containing conductive particles.

As described above, it has been clarified that the biopotential measuring electrode corresponding to the example of the present disclosure exhibits excellent impedance characteristic and enables highly accurate measurement.

Test Example 2

First, copper particles (manufactured by DAIKEN CHEMICAL CO., LTD.) were stirred in an aqueous solution containing about 0.5% of sulfide ions and then dried to modify the surface of the copper particles to form copper sulfide. The obtained particles are conductive particles in which copper particles are used as the base material particles and copper sulfide is present as the surface-treated region.

Separately from the conductive particles described above, the conductive carbon black (TOKABLACK manufactured by TOKAI CARBON CO., LTD., average primary particle diameter (catalog value): 25 nm) was prepared.

The conductive particles obtained as described above were kneaded with a thermoplastic olefin-based elastomer (EXCELINK manufactured by JSR Corporation) so that the content was 30% by mass to obtain a conductive elastomer 1.

Furthermore, the carbon black was kneaded with the thermoplastic olefin-based elastomer (EXCELINK manufactured by JSR Corporation) so that the content was 30% by mass to obtain a conductive elastomer 2.

By injection molding (two-color molding) using the two types of conductive elastomers described above, a flat biopotential measuring electrode was manufactured in which conductive particles were unevenly distributed and the conductive particles were present on the side in contact with the living body. The size of the manufactured biopotential measuring electrode is 1 cm×1 cm×1 cm. Furthermore, the thickness of a portion where the conductive particles were unevenly distributed was about 0.2 cm.

When the impedance characteristic at 10 Hz was measured for the obtained biopotential measuring electrode by using the impedance measuring instrument (CompactStat.h manufactured by Ivium Technologies), the impedance |Z| was 510 Ω·cm$^2$.

In the above, the preferred embodiments of the present disclosure have been described in detail with reference to the accompanying drawings, but the technical scope of the present disclosure is not limited to such examples. It is obvious that persons having ordinary knowledge in the technical field of the present disclosure can conceive various modification examples or correction examples within the scope of the technical idea described in the claims, and it is understood that the modification examples or correction examples also belong to the technical scope of the present disclosure.

Furthermore, the effects described in the present specification are merely illustrative or exemplary and not restrictive. That is, the technology according to the present disclosure can exhibit other effects obvious to those skilled in the art from the description of the present specification together with the above-described effects or in place of the above-described effects.

Note that, the following configurations also belong to the technical scope of the present disclosure.

(1)
A biopotential measuring electrode including
at least a portion in contact with a living body, the portion including:
a base material resin layer containing a predetermined resin material, rubber, or an elastomer, as a main component; and
a conductive particle contained in the base material resin, in which
the conductive particle includes a predetermined base material particle, and a surface-treated region in which at least a part of a surface of the base material particle is coated or substituted with a predetermined material and that exhibits conductivity.

(2)
The biopotential measuring electrode according to (1), in which
the base material particle is a polymer particle, a carbon particle, or a metal particle, and
the surface-treated region is a surface-coated region in which at least a part of a surface of the carbon particle or the metal particle is coated with an organic conductive polymer.

(3)
The biopotential measuring electrode according to (2), in which the organic conductive polymer is at least one selected from the group consisting of PEDOT-PSS, polypyrrole, polyacetylene, polyphenylene vinylene, polythiophene, polythiol, polyaniline, and analogs thereof.

(4)
The biopotential measuring electrode according to (1), in which
the base material particle is a metal particle, and
the surface-treated region is a surface-coated region in which at least a part of a surface of the metal particle is coated with a predetermined metal compound.

(5)
The biopotential measuring electrode according to (4), in which
the metal particle is at least one of a gold particle, a silver particle, or a copper particle, and
the metal compound is at least one of a sulfide, a selenide, or a chloride of gold, silver, or copper.

(6)
The biopotential measuring electrode according to (1), in which
the base material particle is a metal particle, and
the surface-treated region is a surface-modified region in which at least a part of a surface of the metal particle is substituted with a predetermined substituent.

(7)
The biopotential measuring electrode according to (6), in which
the metal particle is at least one of a gold particle, a silver particle, or a copper particle, and
in the surface-treated region, the surface of the metal particle is sulfurized, selenized, or chlorinated.

(8)
The biopotential measuring electrode according to any one of (1) to (7), in which an average particle diameter of the base material particle is within a range of from 10 to 100 nm in primary particle diameter.

(9)
The biopotential measuring electrode according to any one of (1) to (8), in which the conductive particles have an average particle diameter of the conductive particle is within a range of from 15 to 500 nm.

(10)

The biopotential measuring electrode according to any one of (1) to (9), in which a volume resistivity value of the base material resin layer is less than or equal to 100 kΩ·cm.

(11)

The biopotential measuring electrode according to any one of (1) to (10), in which the base material resin layer has a Shore hardness of less than or equal to 90 HS.

(12)

The biopotential measuring electrode according to any one of (1) to (11), in which the base material resin layer contains, as a main component, a thermoplastic resin selected from the group consisting of polyvinyl chloride resin, polypropylene resin, polyethylene resin, polyurethane resin, polyacetal resin, polyamide resin, polycarbonate resin, and copolymers thereof.

(13)

The biopotential measuring electrode according to any one of (1) to (11), in which the base material resin layer contains natural rubber or diene rubber, as a main component.

(14)

The biopotential measuring electrode according to any one of (1) to (11), in which the base material resin layer contains, as a main component, a thermosetting elastomer selected from the group consisting of silicone resin and polyurethane resin.

(15)

A biopotential measuring instrument including at least a biopotential measuring electrode that includes at least a portion in contact with a living body, the portion including: a base material resin layer containing a predetermined resin material, rubber, or an elastomer, as a main component; and a conductive particle contained in the base material resin layer, in which the conductive particle includes a predetermined base material particle, and a surface-treated region in which at least a part of a surface of the base material particle is coated or substituted with a predetermined material and that exhibits conductivity.

REFERENCE SIGNS LIST

10 Biopotential measuring electrode
20 Electrode connection unit
30 Measurement processing unit
101 Base material resin layer
103 Conductive particle
111 Base material particle
113 Surface-treated region
201 Differential amplification unit
203 A/D conversion unit
301 Filter processing unit
303 Sampling processing unit
305 Montage setting unit
307 Arithmetic processing unit
309 Output control unit
311 Storage unit
1000 Biopotential measuring instrument

The invention claimed is:

1. A biopotential measuring electrode, comprising:
a base material resin layer in a portion of the biopotential measuring electrode, wherein
the portion of the biopotential measuring electrode is configured to be in contact with a living body,
the base material resin layer that comprises:
a resin material, rubber, or an elastomer, as a main component; and
a conductive particle, wherein the conductive particle comprises:
a base material particle, and
a surface-treated region in which at least a part of a surface of the base material particle is coated or substituted with a predetermined material that exhibits conductivity, and
an amount of the conductive particles dispersed in a side, of the base material resin layer, that is configured to be closer to the living body is greater than an amount of the conductive particles dispersed on another side of the base material resin layer.

2. The biopotential measuring electrode according to claim 1, wherein the base material particle is a polymer particle, a carbon particle, or a metal particle, and the surface-treated region is a surface-coated region in which at least a part of a surface of the carbon particle or the metal particle or the polymer particle is coated with an organic conductive polymer.

3. The biopotential measuring electrode according to claim 2, wherein the organic conductive polymer is at least one selected from a group consisting of PEDOT-PSS, polypyrrole, polyacetylene, polyphenylene vinylene, polythiophene, polythiol, polyaniline, and analogs thereof.

4. The biopotential measuring electrode according to claim 1, wherein the base material particle is a metal particle, and the surface-treated region is a surface-coated region in which at least a part of a surface of the metal particle is coated with a metal compound.

5. The biopotential measuring electrode according to claim 4, wherein the metal particle is at least one of a gold particle, a silver particle, or a copper particle, and the metal compound is at least one of a sulfide, a selenide, or a chloride of gold, silver, or copper.

6. The biopotential measuring electrode according to claim 1, wherein the base material particle is a metal particle, and the surface-treated region is a surface-modified region in which at least a part of a surface of the metal particle is substituted with a substituent.

7. The biopotential measuring electrode according to claim 6, wherein the metal particle is at least one of a gold particle, a silver particle, or a copper particle, and in the surface-treated region, the surface of the metal particle is sulfurized, selenized, or chlorinated.

8. The biopotential measuring electrode according to claim 1, wherein an average particle diameter of the base material particle is within a range of from 10 to 100 nm in primary particle diameter.

9. The biopotential measuring electrode according to claim 1, wherein an average particle diameter of the conductive particle is within a range of from 15 to 500 nm.

10. The biopotential measuring electrode according to claim 1, wherein a volume resistivity value of the base material resin layer is less than or equal to 100 kΩ·cm.

11. The biopotential measuring electrode according to claim 1, wherein the base material resin layer has a Shore hardness of less than or equal to 90 HS.

12. The biopotential measuring electrode according to claim 1, wherein the base material resin layer contains, as the main component, a thermoplastic resin selected from a group consisting of polyvinyl chloride resin, polypropylene resin, polyethylene resin, polyurethane resin, polyacetal resin, polyamide resin, polycarbonate resin, and copolymers thereof.

13. The biopotential measuring electrode according to claim 1, wherein the base material resin layer contains natural rubber or diene rubber, as the main component.

14. The biopotential measuring electrode according to claim 1, wherein the base material resin layer comprises, as the main component, a thermosetting elastomer selected from a group consisting of silicone resin and polyurethane resin.

15. A biopotential measuring instrument, comprising:
   at least a biopotential measuring electrode that comprises:
      a base material resin layer in a portion of the biopotential measuring electrode, wherein
         the portion of the biopotential measuring electrode is configured to be in contact with a living body,
         the base material resin layer that comprises:
            a resin material, rubber, or an elastomer, as a main component; and
            a conductive particle, wherein the conductive particle comprises:
               a base material particle, and
               a surface-treated region in which at least a part of a surface of the base material particle is coated or substituted with a predetermined material that exhibits conductivity, and
      an amount of the conductive particles dispersed in a side, of the base material resin layer, that is configured to be closer to the living body is greater than an amount of the conductive particles dispersed on another side of the base material resin layer.

* * * * *